United States Patent [19]

Sato et al.

[11] Patent Number: 4,845,301
[45] Date of Patent: Jul. 4, 1989

[54] PROCESS FOR THE PREPARATION OF α-HDROXYKETONES

[75] Inventors: Kazuo Sato; Noritsugu Yamasaki; Ichirou Takase, all of Himeji, Japan

[73] Assignee: Daicel Chemical Industries, Ltd., Osaka, Japan

[21] Appl. No.: 94,152

[22] Filed: Sep. 8, 1987

[30] Foreign Application Priority Data

Sep. 19, 1986 [JP] Japan ............................ 61-219170

[51] Int. Cl.$^4$ ............................................ C07C 45/51
[52] U.S. Cl. .................................. 568/310; 568/384; 568/316; 568/394
[58] Field of Search ............... 568/384, 310, 394, 341, 568/316, 348

[56] References Cited

U.S. PATENT DOCUMENTS 3,236,896  2/1966  Sullivan et al. ..................... 568/384
3,280,191 10/1966  Wheelock ............................ 568/394

FOREIGN PATENT DOCUMENTS 0094347 11/1983  European Pat. Off. ............ 568/308

OTHER PUBLICATIONS

Curtin et al, J.A.C.S., vol. 73, pp. 2633–2636 (1951).
Tada, Chem. Soc. Jap, vol. 1982, p. 2829 (1982).
Craig et al, J. Org. Chem, vol. 37, pp. 3539–3541 (1972).

*Primary Examiner*—James H. Reamer
*Attorney, Agent, or Firm*—Sheldon Palmer

[57] ABSTRACT

A process for the preparation of α-hydroxyketones

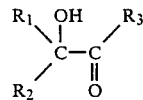

having a high purity in a good yield from a compound

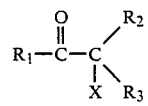

by rearrangement reaction in aqueous alkaline solution, where $R_1$ and $R_3$ each represent an alkyl, alkenyl or aryl group, $R_2$ represents a hydrogen atom or an alkyl, alkenyl or aryl group, and X represents hydroxyl group or a halogen atom.

6 Claims, No Drawings

PROCESS FOR THE PREPARATION OF α-HDROXYKETONES

BACKGROUND OF THE INVENTION

Field of the Invention

The present invention relates to a process for the preparation of α-hydroxyketones. More particularly, it relates to an improved process for the preparation of α-hydroxyketones useful as intermediates in the preparation of medicines or agricultural chemicals, such as 2-hydroxy-3-phenyl-2-butanone which is useful as an intermediate for the synthesis of 4-methyl-4-phenyl-4,5-dihydro-4-oxofuran-2-carboxylic acid, a hypo-lipemia factor (cf. U.S. Pat. Nos. 4,169,202 and 4,244,958).

Brief Description of the Prior Art

Processes for the preparation of α-hydroxy-ketone compounds heretofore known include the following: treatment of an α-hydroxyisobutyrophenone, a compound of general formula (1) as described below, with sodium hydroxide in a mixture of methanol and water (cf. Takashi Toda: Journal of the Chemical Society of Japan, page 282[1982]). In the noted article, however, there is only given a description to the effect that 3-hydroxy-3-phenyl-2-butanone could have been identified by means of infrared absorption spectrum.

As a result of experiments performed according to the process described in the above mentioned journal, we have found that the reaction product contains, besides 3-hydroxy-3-phenyl-2-butanone, a large quantity of compounds which are considered dimerization or polymerization products of the starting materials or the end product, as impurities. Thus, it has become clear that, when the reaction product obtained according to the known process is directly treated, without being isolated and purified, with a sodium hydride and an oxalic acid ester to synthesize 4,5-dihydro-5-methyl-4-oxo-5-phenylfuran-2-carboxylic acid, a hypo-lipemia factor, for example, according to the process described in U.S. Pat. No. 4,169,202, it is necessary to separate from the resulting product those by-products which are formed by side reactions caused by such impurities.

Another known process for the preparation of the compounds of the present invention is a process wherein a compound of the formula (1) is treated in ethanol with potassium hydroxide (cf. D. Y. Curtin: Journal of Organic Chemistry, Vol. 32, page 847[1987] and D. Y. Curtin: Journal of American Chemical Society, Vol. 73, page 2633[1951]). This process, however, attains not necessarily good yields since the final product formed causes further decomposition reactions.

Further, a process wherein acetylene is added to acetaldehyde and the addition product is treated with a mercury salt (cf. the above mentioned U.S. Pat. No. 4,169,202) is also known as a process for the preparation of the compounds of the present invention. This process, using mercury and acetylene, requires one to deal with environmental and safety problems.

SUMMARY OF THE INVENTION

The present invention provides a process for the preparation of α-hydroxyketones of the formula (2)

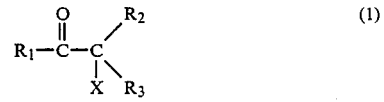

wherein $R_1$ and $R_3$ each represent an alkyl, alkenyl or aryl group, and $R_2$ represents a hydrogen atom or an alkyl, alkenyl or aryl group, from a compound of the formula (1)

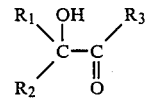

wherein $R_1$, $R_2$ and $R_3$ are as defined above, and X represents hydroxyl group or a halogen atom the process comprising, dispersing a compound of the formula (1) in an aqueous alkaline solution and heating the dispersion to cause the reaction.

According to the process of this invention, α-hydroxyketones having high purity are obtained in good yield.

DESCRIPTION OF THE PREFERRED EMBODIMENTS

In the above definitions, the term alkyl group means a straight or branched chain alkyl group containing 1–8, preferably 1–5 carbon atoms, such as methyl, ethyl, n-propyl, iso-propyl, n-butyl, iso-butyl, tert-butyl, n-octyl, etc.

The term alkenyl group means a straight or branched chain alkenyl group containing 3–5 carbon atoms, such as allyl, 2-butenyl, 2-methylallyl, 1-pentenyl, 2-methyl-2-butenyl, etc.

The term aryl group means an aryl group which may be substituted by straight or branched chain alkyl group(s) containing 1–5 carbon atoms, such as phenyl, tolyl, xylyl, biphenyl, naphthyl, anthryl, phenanthryl, etc.

Further, when $R_1$, $R_2$ and $R_3$ each represent an alkyl group, any two of the alkyl groups may link together to form a ring. An example of such case is 1-hydroxy-2-oxo-1-phenylcycloheptane.

When $R_1$, $R_2$ and $R_3$ each represent an alkyl, alkenyl or aryl, they may be the same group or different from one another.

X is hydroxyl or a halogen atom such as chlorine, bromine, iodine, etc.

Preferred examples of the compounds of the formula (1), which are the starting materials of the present invention, are α-hydroxy-isobutyrophenone, α-chloro-isobutyrophenone, 2-hydroxy-3-oxo-2,4-dimethyl-pentane, 1-hydroxy-2-oxo-1,1-diphenylpropane, 4-chloro-3-oxo-2,2-dimethyl-4-ethylhexane, 3-hydroxy-4-oxo-heptane, 2-hydroxy-2-oxo-1-phenyl-2-(4-chlorophenyl)-propane, 1-hydroxy-1-methyl-3-oxo-5-butene and 1-hydroxy-2-oxo-1-phenyl-cycloheptane.

The aqueous alkaline solution is an aqueous solution of an inorganic alkaline substance such as an alkali metal hydroxide or an alkaline earth metal hydroxide, or such aqueous solution to which an organic solvent which is substantially water insoluble, dissolves the compounds of the formula (1) and is inert to the reaction is added. The alkali metal hydroxides include sodium hydroxide, potassium hydroxide and lithium hydroxide, and the alkaline earth metal hydroxide includes magnesium hydroxide, calcium hydroxide and barium hydroxide. In view of the aspect of reaction velocity and others, the preferred alkaline substance is sodium hydroxide or potassium hydroxide. These alkaline substances may be used also in combination.

The alkaline substance is considered to act as a catalyst in the rearrangement reaction of the present invention. Therefore, the reaction system is required to be substantially alkaline. However, when X in the starting compound of the formula (1) is a halogen atom, the halogen is converted into hydroxyl group by the reaction with the alkaline substance and accordingly the corresponding additional amount of alkali is required.

To be specific, when X in the formula (1) is hydroxyl group, the alkaline substance is used in an amount of 0.02–50 mols, preferably 2–30 mols in view of the reaction velocity, per 1 mol of the compound (1). When X in the formula (1) is a halogen atom, the alkaline substance is used in an amount of 1.02–50 mols, preferably 2–30 mols, per 1 mol of the compound (1).

The concentration of alkali in the aqueous alkaline solution (not containing the organic solvent) is preferably 0.5–8N, in view of the rearrangement ratio and the control of side reactions.

The aqueous alkaline solution may contain an organic solvent which is substantially water insoluble, dissolves the starting substance and is inert to the reaction, up to about 30 v/v %. Such organic solvents include an aromatic hydrocarbon such as benzene, toluene, etc., an aliphatic halo compound such as chloroform, carbon tetrachloride, etc., an aliphatic hydrocarbon such as hexane, pentane, cyclohexane, etc. and an aliphatic ether such as diethyl ether, diisopropyl ether, etc.

In the reaction of the present invention, it is required that the starting substance [the compound of the formula (1)] be dispersed in the aqueous alkaline solution. Dispersion means a state in which the compound (1) and the aqueous alkaline solution form an interface so that the rearrangement reaction of the present invention is effected by contact of the compound (1) with the aqueous alkaline solution at the interface. Therefore, it is desirable to form a good dispersion state by stirring the reaction system with a stirrer, because the reaction velocity is increased when the contact area of the two components is increased. When the above-mentioned organic solvent is used, the compound (1) is dissolved in the organic solvent and so the concentration of the compound (1) at the interface of the compound (1) with water is decreased. Accordingly, the use of the organic solvent is effective to prevent by-product formation.

The reaction is effected by heating the dispersion at the boiling point of water or at a temperature below that. The reaction time varies depending on the reaction temperature and the nature of the starting materials. In general, the reaction time is several hours to several days, usually 5–12 hours.

From the reaction mixture thus obtained, α-hydroxyketones of high purity can be isolated by conventional means (for example, extraction with a suitable solvent), without necessitating any purification step.

In the following examples, the present invention is explained in more detail. The invention, however, is not limited to these Examples.

EXAMPLE 1

One gram of α-hydroxy-isobutyrophenone (1a) was dispersed in 25 ml of 2N-aqueous sodium hydroxide solution, and the dispersion was refluxed by heating for 6 hours while stirring. After completion of the reaction, benzene was added to the reaction mixture. From the separated upper layer, the solvent was removed by distillation whereby crude product 3-hydroxy-3-phenyl-2-butanone (2a) was obtained in a crude yield of 97%.

The crude product thus obtained was shown to have a purity of 99.1% by means of gas chromatography analysis [filler: OV 210, length: 2 m, carrier gas: $N_2$, column temperature: 200° C., detection method: heat conductivity type detector (TCD)].

EXAMPLES 2–5

The same procedure as in Example 1 was effected, except that the concentration of sodium hydroxide and the reaction time were changed in each Example. The results obtained are shown in Table 1.

EXAMPLE 6

The reaction of this Example is represented by the following reaction formula 2:

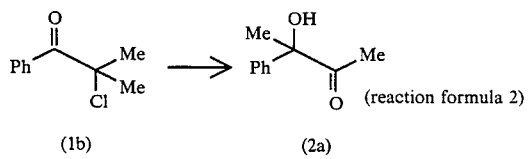

(reaction formula 2)

One gram of α-chloro-isobutyrophenone (1b) was dispersed in 25 ml of 2N-aqueous sodium hydroxide solution, and the dispersion was refluxed by heating for 6 hours while stirring. Then, the same procedure as in Example 1 was effected. The result is shown in Table 1. In this example, "Ph" indicates phenyl and "Me" indicates methyl.

EXAMPLE 7

One gram of 2-hydroxy-3-oxo-2,4-dimethyl-pentane was dispersed in 25 ml of 2N-aqueous potassium hydroxide solution, and the dispersion was refluxed by heating for 6 hours while stirring. After completion of the reaction, the reaction mixture was treated in the same manner as in Example 1 whereby 3-hydroxy-4-oxo-2,3-dimethyl-pentane was obtained. The result is shown in Table 1.

EXAMPLE 8

One gram of 4-chloro-3-oxo-2,2-dimethyl-4-ethyl-hexane was dispersed in 25 ml of 2N-aqueous calcium hydroxide solution, and the dispersion was refluxed by heating for 6 hours while stirring. After completion of the reaction, the reaction mixture was treated in the same manner as in Example 1 whereby 3-hydroxy-4-oxo-2,2-dimethyl-3-ethyl-hexane was obtained. The result is shown in Table 1.

EXAMPLE 9

One gram of 1-hydroxy-2-oxo-1,1-diphenyl-propane was dispersed in 25 ml of 2N-aqueous potassium hydroxide solution, and the same procedure as in Example 1 was effected whereby 2-hydroxy-1-oxo-1,2-diphenyl-propane was obtained. The result is shown in Table 1.

EXAMPLE 10

One gram of 1-hydroxy-2-benzoyl-cyclopentane was dispersed in 25 ml of 2N-aqueous sodium hydroxide solution, and the same procedure as in Example 1 was effected whereby 1-hydroxy-2-oxo-1-phenyl-cyclohexane was obtained. The result is shown in Table 1.

COMPARATIVE EXAMPLE

T. Toda's process [Journal of the Chemical Society of Japan, page 282(1982)]

In a mixture of 5 ml of methanol and 10 ml of 4N-aqueous sodium hydroxide solution was dissolved 0.5 of α-hydroxyisobutyrophenone, and the resulting solution was refluxed by heating for 5 hours. Then, the same procedure as in Example 1 was effected. The result is shown in Table 1.

TABLE 1

|  | Alkali Concentration (Normal) | Reaction Time (hours) | Crude Yield (%) | Purity[1] (%) | High Molecular Compounds such as Dimer etc.[2] (%) |
| --- | --- | --- | --- | --- | --- |
| Comparative Example | 4 | 5 | 88 | 80 | 9 |
| Example 1 | 2 | 6 | 97 | 99.1 | not detectable |
| Example 2 | 4 | 6 | 99 | 99.0 | 0.1 |
| Example 3 | 4 | 12 | 93 | 97.2 | 0.1 |
| Example 4 | 0.5 | 6 | 99 | 97.3 | not detectable |
| Example 5 | 0.5 | 12 | 82 | 99.2 | " |
| Example 6 | 2 | 6 | 80 | 99.6 | " |
| Example 7 | 2 | 6 | 97.3 | 99.0 | " |
| Example 8 | 2 | 6 | 98.4 | 99.1 | " |
| Example 9 | 2 | 6 | 92.0 | 99.4 | " |
| Example 10 | 2 | 6 | 90.8 | 99.1 | " |

[1] The purity was determined by means of gas chromatography, as in Example 1.
[2] The content (%) was pursued from the peak area ratio in gas chromatography.

From the above Examples and the comparative Example, it is evident that, when the same starting material is used, the process of this invention exhibiting a purity-converted yield of 81.3–96.3% (Examples 1–5) is superior to the known process exhibiting a purity-converted yield of 70.4% (Comparative Example).

Also when a different material is used, the product having a high purity is obtained without any dimer detected, in a purity-converted yield of 79.7–97.4%.

What we claim is:

1. A process for the preparation of α-hydroxyketones of the formula (2):

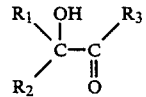

(2)

wherein $R_1$, $R_2$ and $R_3$ are defined below in formula (1) from a compound of the formula (1):

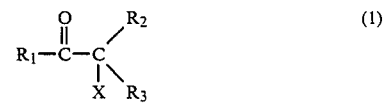

wherein $R_1$, $R_2$ and $R_3$ are each $C_{1-8}$ alkyl, $C_{3-5}$ alkenyl or an aryl group provided that at least one of $R_1$ and $R_2$ is $-CH_2R_4$, wherein $R_4$ is hydrogen or $C_{2-7}$ alkyl and X is hydroxyl group, said process comprising heating a dispersion of the compound of the formula (1) in an aqueous alkaline solution having an alkali concentration of 0.5 to 8N at a temperature up to the boiling point of water.

2. A process as claimed claim 1, wherein the alkaline substance in the aqueous alkaline solution is an alkali metal hydroxide or an alkaline earth metal hydroxide.

3. A process as claimed in claim 2, wherein the alkali metal hydroxide is sodium hydroxide or potassium hydroxide.

4. A process as claimed in claim 1, wherein the alkaline substance is used in an amount of 0.02–50 mols per mol of the compound of the formula (1).

5. A process as claimed in claim 1, wherein the heating is conducted under stirring.

6. A process as claimed in claim 1, wherein the compund of the formula (1) is α-hydroxy-isobutyrophenone, 2-hydroxy-3-oxo-2,4-dimethylpentane, 1-hydroxy-2-oxo-1,1-diphenyl-propane or 1-hydroxy-1-benzoylcyclopentane.

* * * * *